(12) United States Patent
Karaus et al.

(10) Patent No.: US 7,029,175 B2
(45) Date of Patent: Apr. 18, 2006

(54) METHOD AND APPARATUS FOR OBJECT COLLISION DETECTION UTILIZING A PID CONTROLLER IN A MOTORIZED, MOBILE C-ARM

(75) Inventors: Brett Alan Karaus, Salt Lake City, UT (US); John Matthew Simmons, West Jordan, UT (US); David Ellis Barker, Salt Lake City, UT (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 90 days.

(21) Appl. No.: 10/440,821

(22) Filed: May 19, 2003

(65) Prior Publication Data

US 2004/0234039 A1    Nov. 25, 2004

(51) Int. Cl.
*H05G 1/08* (2006.01)
*G05B 19/18* (2006.01)

(52) U.S. Cl. .................. 378/197; 378/91; 700/255

(58) Field of Classification Search .......... 378/91, 378/117, 193, 196, 197, 198; 700/255, 177
See application file for complete search history.

(56) References Cited

U.S. PATENT DOCUMENTS

| | | | | |
|---|---|---|---|---|
| 5,485,502 A * | 1/1996 | Hinton et al. | ............... | 378/117 |
| 5,583,909 A | 12/1996 | Hanover | ............... | 378/197 |
| 5,651,044 A | 7/1997 | Klotz | ............... | 378/117 |
| 5,710,496 A | 1/1998 | Boom | ............... | 318/610 |
| 6,334,708 B1 * | 1/2002 | Kosugi | ............... | 378/197 |
| 6,408,051 B1 * | 6/2002 | Habraken et al. | ............... | 378/117 |
| 6,430,259 B1 * | 8/2002 | Meek et al. | ............... | 378/117 |
| 6,508,586 B1 * | 1/2003 | Oota | ............... | 378/196 |
| 6,830,375 B1 * | 12/2004 | Deshpande | ............... | 378/197 |
| 6,920,370 B1 * | 7/2005 | Wehrli et al. | ............... | 700/177 |
| 2001/0012973 A1 | 8/2001 | Wehrli et al. | ............... | 700/193 |
| 2004/0042587 A1 * | 3/2004 | Deshpande | ............... | 378/198 |
| 2004/0125918 A1 * | 7/2004 | Shanmugavel et al. | .... | 378/98.8 |
| 2005/0088132 A1 * | 4/2005 | Curtis | ............... | 318/610 |

FOREIGN PATENT DOCUMENTS

| | | |
|---|---|---|
| EP | 0459717 A1 | 12/1991 |
| EP | 0588418 A1 | 3/1994 |
| EP | 1243242 A1 | 9/2002 |

* cited by examiner

*Primary Examiner*—Allen C. Ho
(74) *Attorney, Agent, or Firm*—McAndrews, Held & Malloy, Ltd.; Peter J. Vogel; Michael A. Dellapenna (57) ABSTRACT

Certain embodiments of the present invention relate to a collision detection system. The collision detection system includes a position indicator for determining an actual position of a component connected to the collision detection system. The system also includes an error calculator for determining a position error between the actual position and a selected position. The system further includes a comparator for comparing the position error to a position error limit. The comparator generates a halt signal based on the position error and position error limit. The system also includes a motion controller for controlling motion of the component. The motion controller stops motion of the component based on the halt signal. The comparator generates a halt signal when the position error is equal to or greater than the position error limit.

13 Claims, 8 Drawing Sheets

METHOD AND APPARATUS FOR OBJECT COLLISION DETECTION UTILIZING A PID CONTROLLER IN A MOTORIZED, MOBILE C-ARM

RELATED APPLICATIONS

[Not Applicable]

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

The present invention generally relates to detecting a collision between a movable component of an imaging system and an object. In particular, the present invention relates to object collision detection using a Proportional Integral Derivative (PID) controller on a motorized, mobile C-Arm.

Medical diagnostic imaging systems encompass a variety of imaging modalities, such as x-ray systems, computerized tomography (CT) systems, ultrasound systems, electron beam tomography (EBT) systems, magnetic resonance (MR) systems, and the like. Medical diagnostic imaging systems generate images of an object, such as a patient, for example, through exposure to an energy source, such as x-rays passing through a patient, for example. The generated images may be used for many purposes. For instance, internal defects in an object may be detected. Additionally, changes in internal structure or alignment may be determined. Fluid flow within an object may also be represented. Furthermore, the image may show the presence or absence of objects in an object. The information gained from medical diagnostic imaging has applications in many fields, including medicine and manufacturing.

Radiation imagers, such as x-ray machines, are typically accurately positioned close to a patient or object to be imaged in order to provide desired imaging information. One type of radiation imager is a mobile C-arm system. In the medical field, the mobile C-arm system may be used for general surgery, orthopedic procedures, pain management procedures, vascular procedures, and cardiac procedures, for example. Typically, the mobile C-arm has an x-ray source mounted at one end of a mainframe and a detector, such as an image intensifier, mounted at the other end of the mainframe. The mobile C-arm may be moved in relation to the object, such as a patient, to be imaged.

Motorized motion of any of the axes of a mobile C-arm system poses possible risks to the patient and to the imaging system and other equipment. It is desirable to prevent or minimize collisions between the mobile C-arm and an object, such as the patient. A possibility of collision exists whether the C-arm is moved through automated trajectory tracking or through direct user input from a user interface device. It is therefore desirable to prevent or minimize collisions when the mobile C-arm is controlled by both an external user and by an automated system or program. A method and system for minimizing collisions that do occur would also be highly desirable.

Imaging systems typically use one of two types of anti-collision sensors: contact sensors and proximity sensors. A proximity sensor detects the presence of an object within a given distance from a movable part of the C-arm imaging apparatus. A proximity sensor may be a capacitive proximity sensor. Current proximity sensors are limited by the complexity of electronic circuitry. Complex, additional electrical circuitry impacts the cost, maintenance, and performance, for example, of the imaging system. Current sensor systems are also limited by distances between sensors and imaging system components. That is, operating constraints limit the distance between a proximity sensor and an image intensifier, for example. Furthermore, capacitive proximity sensing has not been used with a mobile C-arm apparatus.

Another type of collision sensor is a contact sensor. A contact sensor may use a bumper, for example. The contact sensor detects a change in a signal resulting when the bumper contacts an object. Typically, the contact sensor detects a change in pressure from contact with the object.

However, current systems may misinterpret a collision as an error in system performance. Misinterpretation may result in more power being applied to motors in the motorized C-arm system. Eventually, the system may apply the maximum power available and, thus, apply maximum torque to the system. High torque may result in unacceptably high forces exerted on the collided object.

Thus, a need exists for an improved method and system for object collision detection on a motorized, mobile C-arm system.

BRIEF SUMMARY OF THE INVENTION

Certain embodiments of the present invention provide a method and system for improved collision detection in a mobile, motorized C-arm imaging system. In a certain embodiment, the system includes a moveable C-arm for positioning an x-ray source and an x-ray receptor, a position indicator for determining an actual position of the C-arm, an error calculator for determining a position error between the actual position of the C-arm and a selected position, a comparator for comparing the position error to a position error limit, and a motion controller for controlling motion of the C-arm. The comparator outputs a halt signal based on the position error and the position error limit. The motion controller halts the movement of the C-arm based on the halt signal.

In an embodiment, the halt signal is output when the position error is equal to or greater than the position error limit. Alternatively, the halt signal may be output when the position error is equal to or greater than the position error limit for more than a predefined amount of time. In an embodiment, the error calculator determines the position error by subtracting the actual position from the selected position. In an embodiment, the selected position is determined using at least one of a user interface and an automated control.

The position indicator may be an encoder, for example. The motion controller may be a Proportional Integral Derivative (PID) controller, for example. The position error limit may be a single value, a table of values, and/or a mathematical function, for example.

The system may also include a motor for driving the C-arm. The motor receives a control signal from the motion controller. The system may also include a master control unit. The master control unit transmits commands to the motion controller. The master control unit receives a halt signal from the comparator and transmits a halt command to the motion controller.

Certain embodiments of the method include determining a current position of a C-arm and calculating a position error between the current position and a desired position. The method also includes comparing the position error to a position error limit and generating a control signal to stop the C-arm when the position error is equal to or greater than the position error limit. In an embodiment, the position error may be calculated by subtracting the actual position from the desired position. Additionally, the position error limit may be determined using a single value, a table of values, and/or a mathematical function. The desired position may be determined using a user interface and/or an automated control.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

For the purpose of illustration only, the following detailed description references a certain embodiment of an x-ray imaging system using a mobile, motorized C-arm. It is understood that the present invention may be used with other imaging systems.

Figure 1:
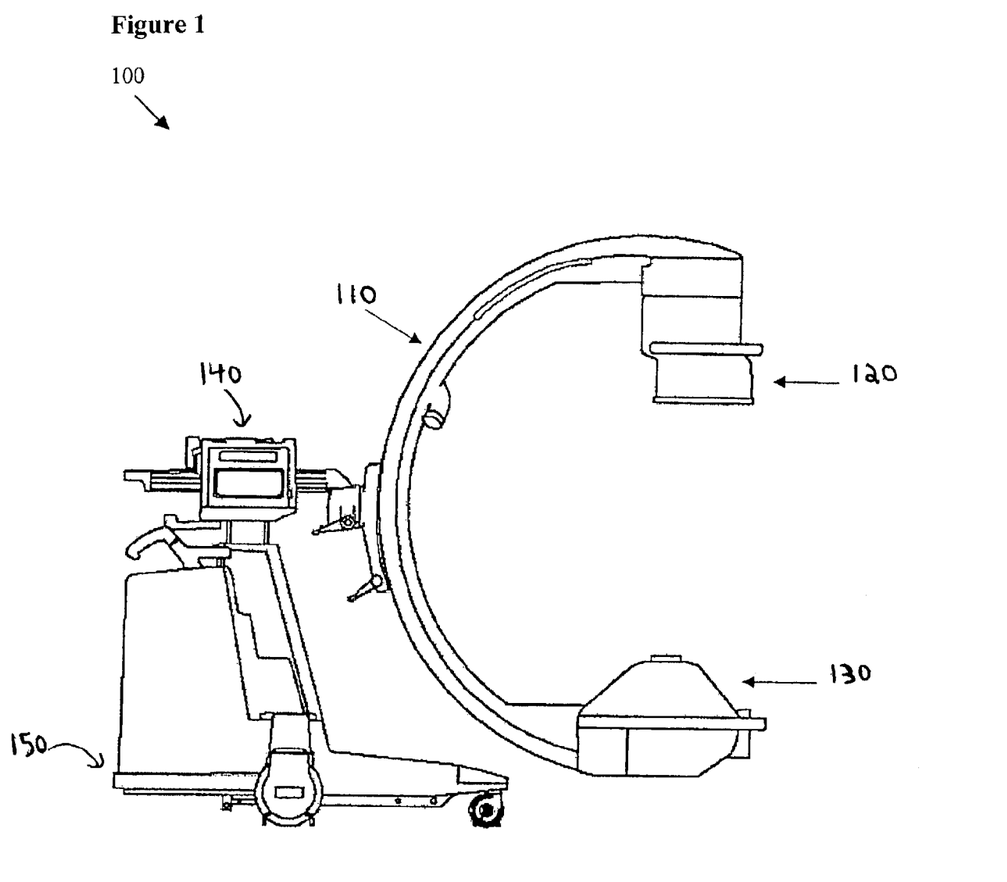
FIG. 1 illustrates a mobile C-arm imaging system used in accordance with certain embodiments of the present invention.

FIG. 1 illustrates a mobile C-arm imaging system 100 used in accordance with certain embodiments of the present invention. The system 100 includes a C-arm 110, an image receptor 120, an x-ray source 130, a support structure 140, and a wheeled base 150. The image receptor 120 and the x-ray source 130 are mounted at opposing locations on the C-arm 110. The support structure 140 provides support for the C-arm 110 and holds the C-arm 110 in a suspended position. The support structure 140 is mounted on a wheeled base 150 that allows the system 100 to be moved. An example of a mobile C-arm imaging system is described in further detail in U.S. Pat. No. 5,583,909, which is herein incorporated by reference.

The support structure 140 provides stable, balanced support for the C-arm 110. The support structure 140 suspends the C-arm 110 for use in imaging a patient or an object, for example. The support structure 140 also allows the C-arm 110 to be rotated about an axis of rotation (manually or using a motor, for example). The support structure 140 is attached to a wheeled base 150, for example, to reposition the mobile C-arm imaging system 100.

The C-arm 110 allows the image receptor 120 and the x-ray source 130 to be mounted and positioned about an object to be imaged, such as a patient. The C-arm 110 may be a circular C-shaped or an arc-shaped member, for example. The C-arm 110 enables selective positioning of the image receptor 120 and the x-ray source 130 with respect to the width and length of the patient or other object located within the interior free space of the C-arm 110.

The image receptor 120 may be an image intensifier or other energy receptor for using in diagnostic imaging, for example. The image receptor 120 and the x-ray source 130 are mounted at opposing positions on the C-arm 110. The image receptor 120 and the x-ray source 130 may be positioned about an object, such as a patient, using the C-arm 110 and support structure 140. The image receptor 120 and the x-ray source 130 are used to generate a diagnostic image representative of the object being imaged.

In operation, a patient, for example, is placed on a table that is positioned between the image receptor 120 and the x-ray source 130 mounted on the C-arm 110. The support structure 140 moves the C-arm 110. Moving the C-arm 100 positions the image receptor 120 and the x-ray source 130 at desired locations with respect to the patient. The image receptor 120 may be positioned near the patient in order to improve resulting image quality.

Certain embodiments of the present invention provide for a contact sensor that may be used, for example, with a mobile C-arm imaging system, such as the one described above in relation to FIG. 1. Moving the image receptor 120 close to the patient or other object to improve image quality increases a risk of collision between the image receptor 120 or other part of the C-arm 110 and the patient, table, or other object. Certain embodiments detect a collision between the system 100 and the patient or other object being examined. Collision detection is performed to prevent further errors in the system 100 due to impact and overcompensation of the C-arm system 100.

Figure 2:
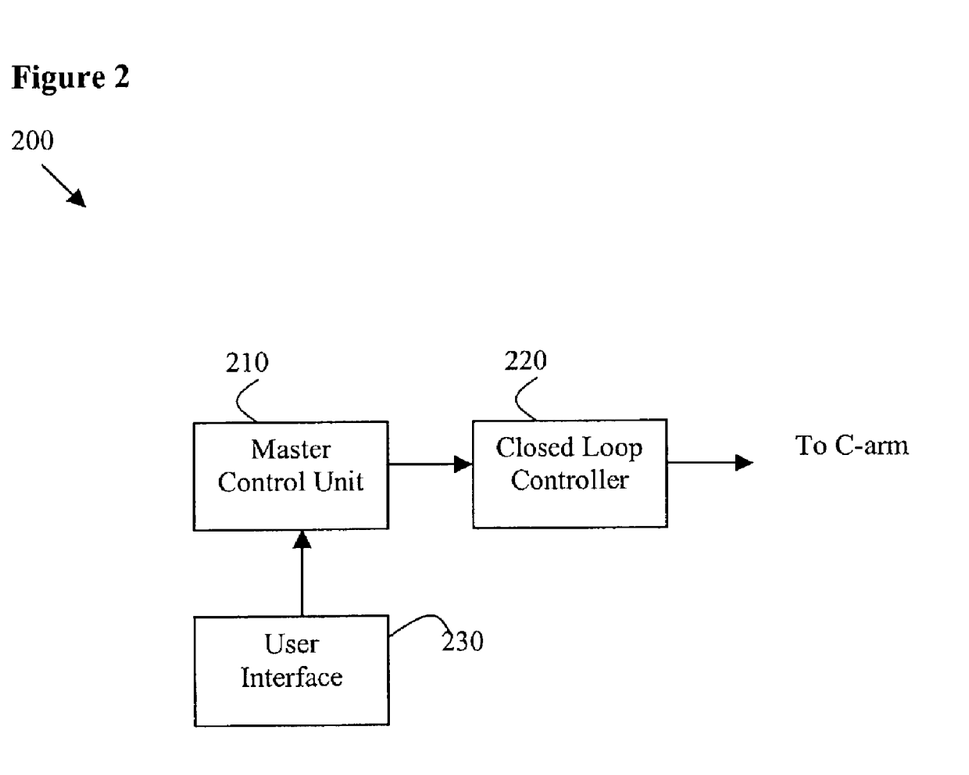
FIG. 2 illustrates a motorized C-arm system controller in accordance with an embodiment of the present invention.

FIG. 2 illustrates a motorized C-arm system controller 200 in accordance with an embodiment of the present invention. The controller 200 includes a master control unit 210, a closed loop controller 220, and a user interface 230. The controller 200 connects to a C-arm system, such as the C-arm system 100. The closed loop controller 220 may include a Proportional Integral Derivative (PID) motion control loop or other control loop.

In operation, a user enters commands via the user interface 230. The user commands are transmitted to the master control unit 210. The master control unit 210 sends a position command to the closed loop controller 220. The closed loop controller 220 then transmits a control signal to the C-arm system 100.

Figure 3:
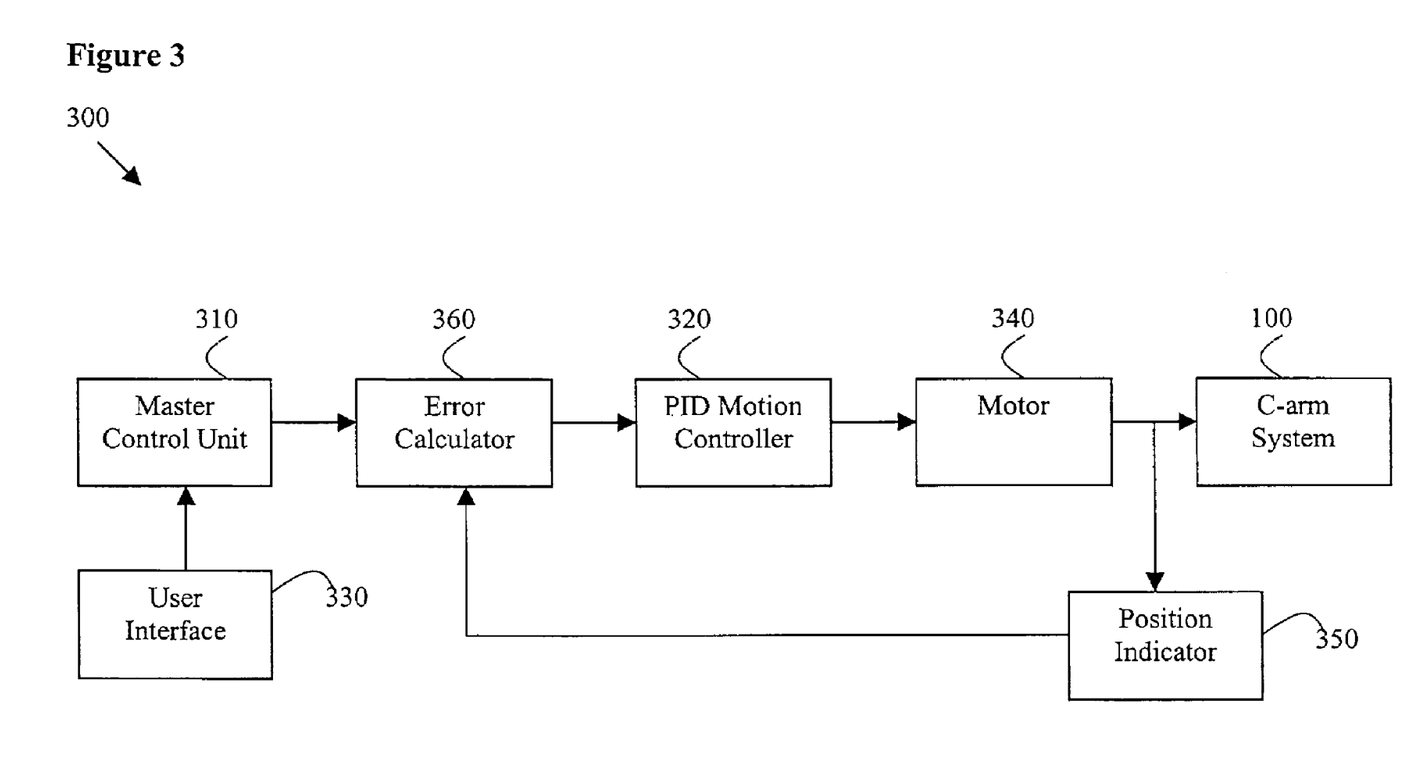
FIG. 3 shows another embodiment of a C-arm system controller used in accordance with an embodiment of the present invention.

FIG. 3 shows another embodiment of a C-arm system controller 300 used in accordance with an embodiment of the present invention. The system controller 300 includes a master control unit 310, a PID motion controller 320, a user interface 330, a motor 340, a position indicator 350, and an error calculator 360 connected to the C-arm system 100. Certain embodiments utilize a position error value for collision detection on a mobile imaging system, such as a mobile C-arm system. An absolute value of a continuous position error value during motion of a component, such as a C-arm 110, may be compared to a preset value. Motion may be halted or slowed if the position error value exceeds the preset value. The operation of the controller 300 is similar to the operation of the controller 400 which is described below.

In a conventional system, the PID motion controller 320 interprets a collision as a performance error in the system 100. As a result, the PID motion controller applies more power to the motor 340 in an attempt to correct performance. However, increasing motor 340 power increases torque on the system 100. Increased torque results in exertion of force on an object that has collided with a part of the system 100, such as the C-arm 110.

Figure 4:
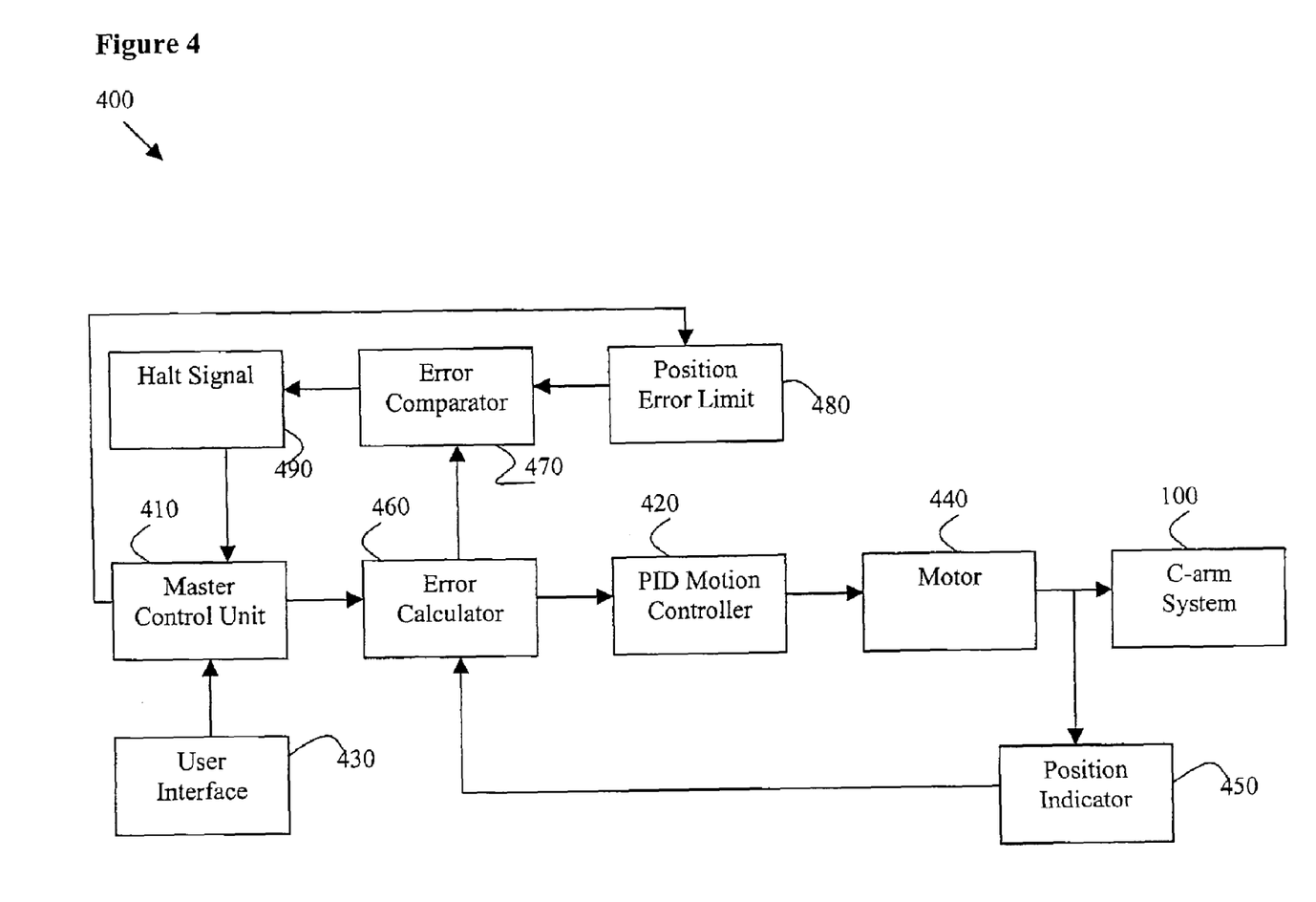
FIG. 4 illustrates a C-arm system controller used in accordance with an embodiment of the present invention.

FIG. 4 illustrates a C-arm system controller 400 used in accordance with an embodiment of the present invention. The system controller 400 is similar to the C-arm system controller 300 described in relation to FIG. 3. The system controller 400 includes a master control unit 410, a PID motion controller 420, a user interface 430, a motor 440, a position indicator 450, an error calculator 460, an error comparator 470, a position error limit 480, and a halt signal 490.

The C-arm system controller 400 (as well as the controllers 200 and 300 described above) may also be used with other systems and other components of imaging systems to detect collisions between system components and other objects. In an alternative embodiment, the PID motion controller 420 may be replaced with another motion controller. The components of the controller 400 (as well as the controllers 200 and 300) may be implemented in hardware and/or in software. The components may be implemented individually or may be combined.

The position error limit 480 may be a single value, a table of values, or a mathematical function, for example. The table of position error values may be driven by other system measurements or parameters. In an embodiment, when a collision occurs, a difference between a position error and the position error limit 480 corresponds to an amount of force applied to a collided object by a component of the system 100, such as the C-arm 110, for a given PID controller 420 setting. The position error limit 480 is used as a force limit to determine when a collision has occurred. As the difference between the position error and the position error limit 480 increases, the amount of applied force increases (e.g., the component is strongly impacting an object). Conversely, as the difference between the position error and the position error limit decreases, the collision force decreases (e.g., the component is no longer impacting the object).

Figure 5:
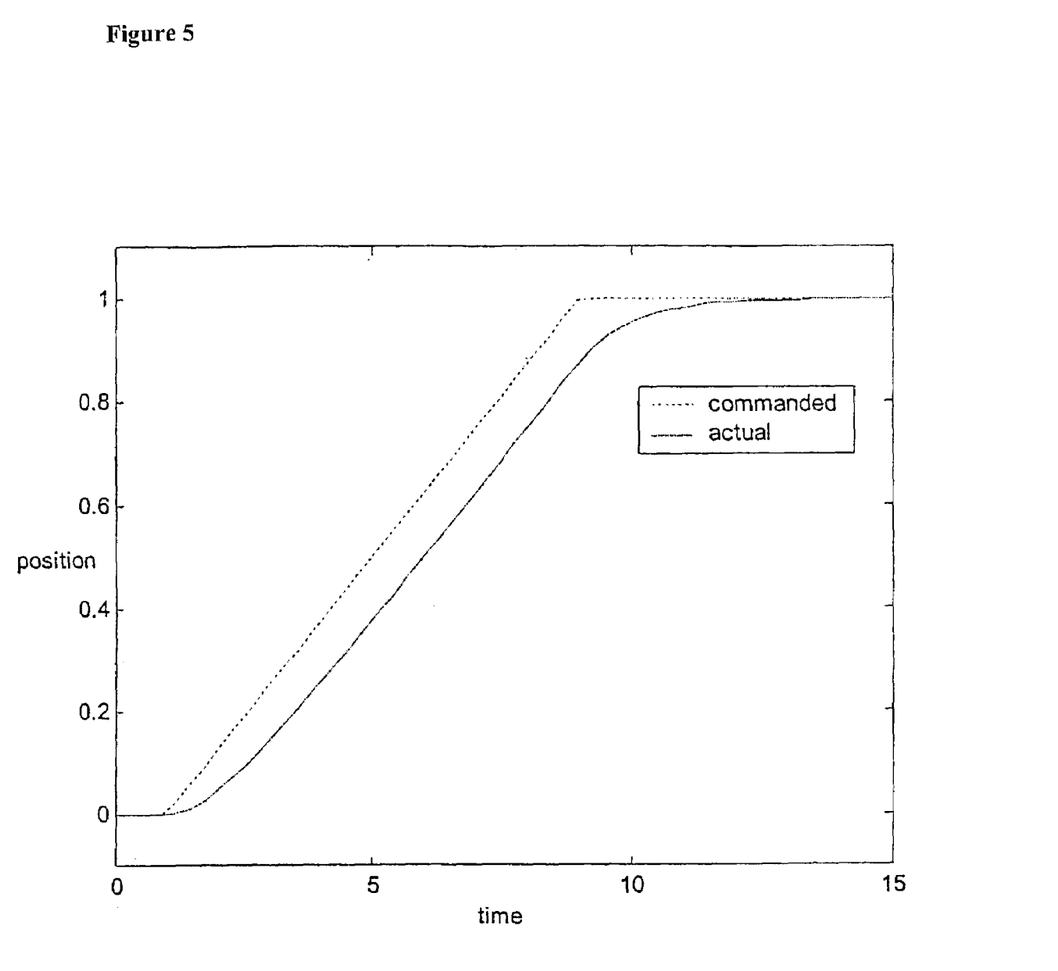
FIG. 5 illustrates a plot of commanded C-arm position versus actual C-arm position for an arbitrary C-arm system in accordance with an embodiment of the present invention.

FIG. 5 illustrates a plot of commanded or desired C-arm 110 position versus actual C-arm 110 position for an arbitrary C-arm system in accordance with an embodiment of the present invention. FIG. 5 illustrates a comparison between a desired position entered by a user and an actual position measured by the position indicator 450. FIG. 5 shows the position error between the commanded and actual positions of the C-arm 110 over time.

Figure 6:
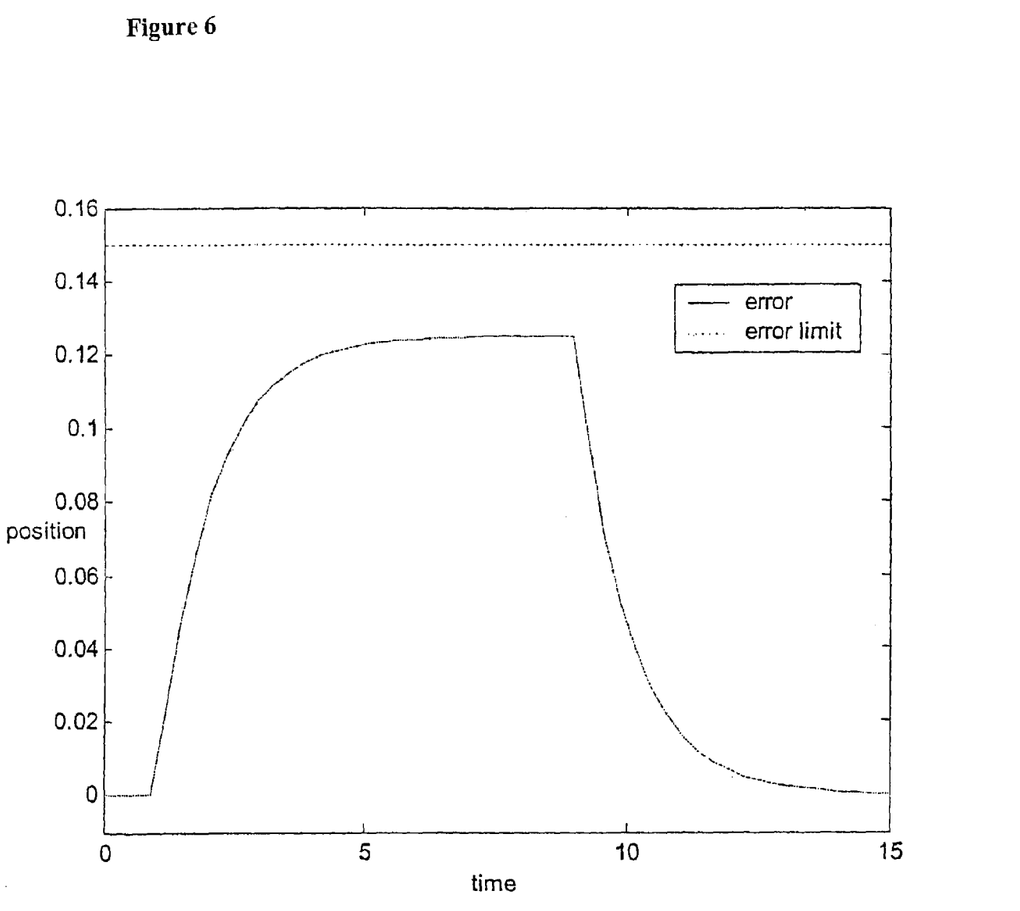
FIG. 6 depicts a position error signal with respect to a position error limit for an arbitrary C-arm system in accordance with an embodiment of the present invention.

FIG. 6 depicts the position error signal calculated in FIG. 5 with respect to the position error limit 480 for an arbitrary C-arm system 100 in accordance with an embodiment of the present invention. In FIG. 6, the position error signal does not exceed the defined position error limit 480. Thus, no collision is detected during motion in FIG. 6.

Figure 7:
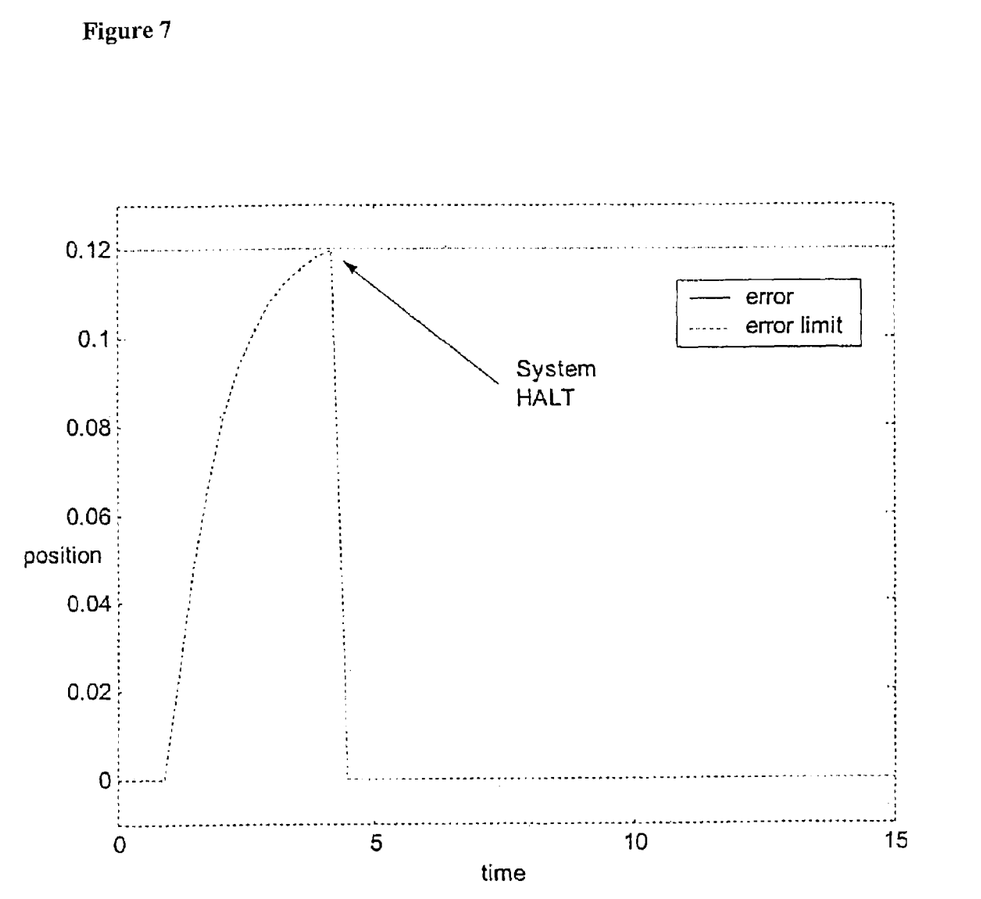
FIG. 7 shows a position error signal compared to a position error limit in accordance with an embodiment of the present invention.

In FIG. 7, the position error limit 480 is lowered from the limit used in FIG. 6. FIG. 7 shows the position error signal reaching the position error limit 480. A position error equal to the maximum position error limit 480 indicates that the C-arm 110 has collided with another object that is impeding the motion of the C-arm 110. When the position error equals or exceeds the position error limit 480, the system 100 is halted to correct for a collision.

A PID controller, such as the PID controller 420, is a feedback-based controller. The PID controller 420 produces an output motion control signal based on an input signal. In an embodiment, the PID controller 420 produces an output based on error between a measured position value and a defined limit. The PID controller 420 receives the position error signal. The PID controller 420 generates a motion control signal for the motor 440 using the position error signal and a signal from the motor control unit 410.

In operation, a user transmits commands to the system 100 via a user interface. For example, the user may select a desired position for the C-arm 110 via the user interface 430 or may initiate C-arm motion or tracking. The user commands are transmitted to the master control unit 410. The master control unit 410 then forwards the commands to the PID motion controller 420. The PID motion controller 420 may be used for motion control on two motorized axes, for example, of the C-arm system 100. The PID controller 420 sends a control signal to the motor 440. The motor 440 may move the orbital and/or rotational axis, for example, of the C-arm 110.

The error calculator 460 compares a current position of the motor 440 from the position indicator 450 to a desired position of the motor 440 and generates a position error signal. The position indicator 450 may be mounted on the shaft of the motor 440, for example. In an embodiment, the position indicator 450 is an encoder, such as an optical encoder. The encoder measures position in encoder counts. For example, an encoder may produce 4000 counts per rotation of the shaft of the motor 440. In an embodiment, the encoder sends a pulse signal to an encoder translator. The translator maintains an absolute value of the encoder counts and converts the pulse signal to a position signal. The position signal is then sent to an error calculator 460. The error calculator 460 generates a position error signal. In an embodiment, the error calculator 460 may subtract the position signal from the desired position signal to determine the position error signal. In an embodiment, the position error corresponds to a number of encoder counts (400 to 2000 encoder counts, for example). The position error signal is fed back into the PID controller 420 to complete a control loop for the C-arm system controller 400. The PID controller 420 may calculate a new control signal for the motor 440 based on the position error signal.

The position error signal and the position error limit 480 are fed into the error comparator 470. The error comparator 470 compares the position error with the position error limit 480. In an embodiment, when an absolute value of the position error exceeds the position error limit 480 for a predefined period of time (for example, 50 milliseconds), a halt signal 490 is generated. The halt signal 490 is transmitted to the master control unit 410. The master control unit 410 instructs the PID controller 420 to stop motion of the system 100. In an embodiment, the position error limit 480 is continually adjusted based on axis position and speed in the C-arm system 100. Error values corresponding to a desired stopping force may be loaded in the master control unit 410. The master control unit 410 may adjust the position error limit 480.

Figure 8:
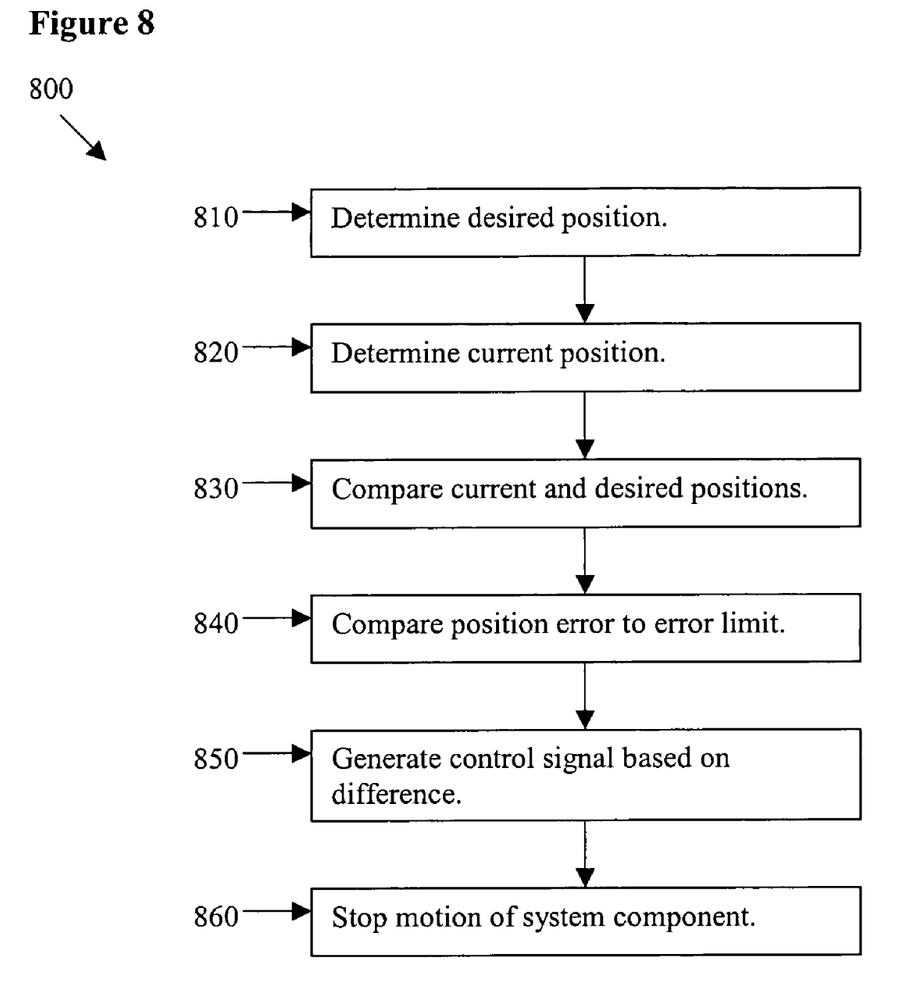
FIG. 8 illustrates a method for collision detection in a mobile C-arm system used in accordance with an embodiment of the present invention.

FIG. 8 illustrates a method 800 for collision detection in a mobile C-arm system 100 in accordance with an embodiment of the present invention. First, at step 810, a desired position for a system component, such as the C-arm 110, is determined. For example, a user may specify the desired position using the user interface 430. Alternatively, an automated control system or program may determine the desired position. Then, at step 820, the current position of the system component, such as the C-arm 110, is determined. For example, an encoder may read the position of the C-arm 110.

Next, at step 830, the current or actual position of the C-arm 110 is compared to the desired or selected position. For example, a user or automated input may select or otherwise command the C-arm 110 to a desired position. The desired position may be compared to the measurement of position from the encoder, for example. A position error is determined by comparing the current and desired positions. For example, the current position may be subtracted from the desired position to calculate the position error. If an encoder is used, for example, the measured encoder count may be subtracted from the desired encoder count to determine the position error.

Then, at step 840, the position error is compared to a predetermined error limit. The error limit may be a single value, a table of values, or a mathematical function, for example. At step 850, a control signal is generated based on the comparison between the position error and the error limit. In an embodiment, a control or halt signal 490 is generated if the position error is greater than the error limit. Alternatively, a control or halt signal 490 is generated if the position error is greater than or equal to the error limit. Finally, at step 860, motion of the system component, such as the C-arm 110, is stopped based on the halt control signal 490. The motion of the C-arm, for example, also stops when the desired position is reached. Motion of the system component may be initiated again after the collision is remedied. Additionally, the position error limit 480 and the predefined time interval may be adjusted (by the master control unit 410, for example) to provide finer or coarser collision detection.

For example, in an embodiment, a patient is positioned on an x-ray table for x-ray imaging. A technician executes a scanning sequence and uses the user interface 430 to move the C-arm 110 in position for proper alignment of the x-ray source 130 and image receptor 120. The technician's position commands are transmitted from the user interface 430 to the master control unit 410. The master control unit 410 sends the commanded C-arm 110 position to the PID controller 420. The PID controller 420 sends motion control signals to the motor 440, which moves the C-arm 110. The position indicator 450 transmits the position of the C-arm 110 back to the PID controller 420 for use in further motion control. If the C-arm 110 hits the patient table, the current position of the C-arm 110, as recorded by the position indicator 450, will begin to lag behind the expected or commanded position given by the master control unit 410. The difference in position, computed by the error calculator 460 and the error comparator 470, will be transmitted to the PID controller 420. The PID controller 420 will adjust the control signals sent to the motor 440 based on the position error information. After a defined time interval indicating that a collision is presumed to have occurred rather than another error, the error comparator 470 will generate a halt signal 490. The master control unit 410 will receive the halt signal 490, which will override the commanded position signal. The master control unit 410 will instruct the PID controller 420 to stop the motor 440. The PID controller 420 will reduce the motor speed to zero to prevent damage to the system 100, the patient table, or the patient. Once the obstruction has been removed or the collision otherwise remedied, new commands may be transmitted to the master control unit 410 for moving the C-arm 110.

Thus, certain embodiments of the present invention provide for a system and method for improved collision detection that utilizes existing system control loops and control signals. Certain embodiments eliminate the need for costly and bulky additional control loops and circuitry. Certain embodiments prevent a controller from applying maximum power in a mistaken attempt to correct system movement in the event of a collision. Certain embodiments minimize the force exerted on a collided object and disruption or damage to the system and the collided object.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A C-arm system with improved collision detection, said system comprising:
   a moveable C-arm for positioning an x-ray source and an x-ray receptor;
   a position indicator for determining an actual position of said C-arm;
   an error calculator for determining a position error between said actual position of said C-arm and a selected position, said selected position determined using at least one of a user interface and an automated control;
   a comparator for comparing said position error to a position error limit, said comparator outputting a halt signal based on said position error and position error limit; and
   a motion controller for controlling motion of said C-arm, said motion controller halting said C-arm based on said halt signal.

2. The system of claim 1, wherein said halt signal is output when said position error is equal to or greater than said position error limit.

3. The system of claim 2, wherein said halt signal is output when said position error is equal to or greater than said position error limit for more than a predefined amount of time, said predefined amount of time determined using at least one of a user interface and an automated control system.

4. The system of claim 1, wherein said error calculator determines said position error by subtracting said actual position from said selected position.

5. The system of claim 1, wherein said position indicator comprises an encoder.

6. The system of claim 1, wherein said motion controller comprises a Proportional Integral Derivative (PID) controller.

7. The system of claim 1, wherein said position error limit comprises at least one of a single value, a table of values, and a mathematical function, said position error limit adjusted at least once based at least in part on at least one of the position of said C-arm and the speed of said C-arm.

8. The system of claim 1, further comprising a motor for driving said C-arm, said motor receiving a control signal from said motion controller.

9. The system of claim 1, further comprising a master control unit, said master control unit transmitting commands to said motion controller, wherein said master control unit receives said halt signal from said comparator and transmits a halt command to said motion controller.

10. A method for collision detection in a mobile C-arm system, said method comprising:
   determining a current position of a C-arm;
   calculating a position error between said current position and a desired position said desired position determined using at least one of a user interface and an automated control;
   comparing said position error to a position error limit; and
   generating a control signal to stop said C-arm when said position error is equal to or greater than said position error limit.

11. The method of claim 10, wherein said calculating step calculates said position error by subtracting said actual position from said desired position.

12. The method of claim 10, wherein said position error limit is determined using at least one of a single value, a table of values, and a mathematical function, said position error limit adjusted at least once based at least in part on at least one of the position of said C-arm and the speed of said C-arm.

13. The method of claim 10, wherein said control signal is generated when said position error is equal to or greater than said position error limit for more than a predefined amount of time, said predefined amount of time determined using at least one of a user interface and an automated control system.

* * * * *